United States Patent [19]

Schimanski

[11] Patent Number: 4,540,571

[45] Date of Patent: Sep. 10, 1985

[54] COSMETIC AGENT CONTAINING NATURAL YEAST CELL CONTENTS

[75] Inventor: Dieter Schimanski, Herzogenrath, Fed. Rep. of Germany

[73] Assignee: Dr. Babor GmbH & Co., Aachen, Fed. Rep. of Germany

[21] Appl. No.: 422,093

[22] Filed: Sep. 23, 1982

[30] Foreign Application Priority Data

Oct. 1, 1981 [DE] Fed. Rep. of Germany ....... 3139093

[51] Int. Cl.$^3$ ...................... A61K 31/78; A61K 35/78
[52] U.S. Cl. ..................................... 424/81; 424/195.1
[58] Field of Search ................................... 424/195, 81

[56] References Cited

U.S. PATENT DOCUMENTS 2,320,478  6/1943  Spenli .................................. 424/195

FOREIGN PATENT DOCUMENTS 870386  10/1942  France .

OTHER PUBLICATIONS

Karl Rothmann, "Das grosse Rezeptbuch der Haut- und Koerperpflegemittel", 4th edition, p. 180, (1969).

Primary Examiner—Albert T. Meyers
Assistant Examiner—John W. Rollins, Jr.
Attorney, Agent, or Firm—Armstrong, Nikaido, Marmelstein & Kubovcik

[57] ABSTRACT

The invention relates to cosmetic agents which contain, besides the usual basic cosmetic substances, natural yeast cell contents. The yeast cell contents are obtained by mechanically breaking open the yeast cell walls and by separating off the cell walls and any cell membranes, employing protective conditions. The invention relates also to extracts of yeast cell contents which contain an enriched fraction of yeast cell nuclei and which, when used in cosmetic agents, have an especially good skin-care effect. The native yeast cell contents comprise the cell contents without the cell walls, or the cell contents without cell walls and without nuclear membranes.

6 Claims, No Drawings

COSMETIC AGENT CONTAINING NATURAL YEAST CELL CONTENTS

DESCRIPTION

The invention relates to a cosmetic agent which is characterized by containing fractions of yeast cell contents.

Yeast is a unicellular plant belonging to the class Ascomycetes, which is very commonly found in nature. This plant is one of the fungus family Saccharomycetaceae. Yeast is taken as a health-giving agent—e.g. in the form of brewers' yeast flakes and tablets, or in dried form—on account of its content of amino acids, minerals, trace elements, vitamins and other active substances. Yeast treatments are supposed to be effective against impure and greasy skin.

It is also known that medicinal yeast can be used as an additive in face packs for treating the facial skin (Karl Rothemann, "Das grosse Rezeptbuch der Haut- und Körperpflegemittel", 4th edition, page 180).

In FR patent No. 870 386 a yeast-containing cosmetic is described which is supposed to improve cutaneous respiration. The yeast is treated for several hours with boiling ethanol, and from the alcoholic filtrate a product—which is not defined more closely—is precipitated with barium hydroxide and incorporated in a cream or soap. The heat treatment with alcohol results in a large proportion of the yeast cell contents being destroyed, i.e. reduced to an inactive, denatured form, as a result of which the health-giving effect of the yeast is considerably impaired.

The invention is accordingly based on the object of providing a cosmetic based on a yeast material, which has skin-care and skin-regenerating properties. The cosmetic agent should moreover regulate the moistness of the skin, tone and smooth the skin and stimulate the blood supply to it.

This objective is established by way of a cosmetic agent which contains, besides the usual cosmetic base substances, fractions of natural yeast cell contents.

The fractions of natural yeast cell contents used according to the invention consist preferably of yeast cell nuclei extracts which are obtained from yeast cells by destroying the cell walls and the cell membranes. The extracts of yeast cell nuclei are for the most part free of yeast cell membranes. They preferably contain desoxyribonucleic acids and the repair complex of the yeast cell nuclei. The basic substances which are normally used in cosmetics and which are used together with the preparation of yeast cell contents are e.g. glycerin, alcohol, polyethylene glycol, scented oils, preservatives, carboxymethyl cellulose, carboxyvinyl copolymer, bees wax, maize germ oil, cholesterol, paraffin oil, magnesium sulphate, decyl oleate, basic ointment substance, polyoxy-ethylated triglyceride, propanol and/or distillated water.

The cosmetic agent according to the invention has very good skin-smoothing and moisture-regulating properties. Roughness of the skin is remedied permanently within a short time if treated with the cosmetic agent of the invention, especially if lotions are used. Soon after treatment with the agents according to the invention, the skin takes on a pleasant silky appearance. Besides the immediate skin-smoothing effect, the cosmetic agents—especially those containing the extracts of yeast cell nuclei—have effective skin-regenerating properties.

The nucleic acids of the yeast join directly in what is happening in the skin cells, thus constituting an effective active substance against cell aging.

The nucleic acids of yeast are rich in hydrophilic groups, which have strong hydrating properties. These acids are probably responsible for forming the moisture-retaining film on the epidermis.

The enzymatic systems of the yeast cell, such as the invertases, break down dead calloused particles, which upset the dermatological balance and the functioning of the sebacious glands. The extracts of yeast cell contents used in the invention therefore have the effect of improving the skin hygiene.

The extract of natural yeast cell contents obtained by smashing the yeast cells contains varying amounts of protein, depending on the starting material. The protein content is generally about 0.5 to 2%. So as to facilitate application, the extract of yeast cell contents is therefore standardized to 1% protein by diluting with the suspension liquid used, e.g. tris buffer.

The cosmetic agents according to the invention contain in particular more than 1 wt. % of cell content extract or fraction (standardized to 1% protein).

It is expedient to use about 2 to 20 wt. %, preferably 5 to 10 wt. % of the extract of yeast cell contents (standardized to 1% protein), relative to the total weight of the cosmetic agent. Higher contents can be used but are not to be recommended for economical reasons.

The extracts of native cell contents according to the invention can be prepared in particular by the following process.

As starting material, all sorts of commercially-available yeasts can be used, especially the Saccharomyces types of yeast such as baker's yeast, brewer's yeast, wine yeast, milk yeast and Torula yeast. The yeast is suspended in distilled water, saline solution, to which saccharose may be added, or in tris buffer solution (tris(hydroxymethyl) amino methane buffer) and then cooled and ground simultaneously. The cells can be broken open e.g. by grinding in normal cell mills or cell bombs, although any other method of breaking open cells can also be used. A vibration grinding mill, e.g., is useful, inside which the bottle containing the yeast suspension is clamped. The bottle contains small balls measuring about 0.2 to 0.5 mm in diameter, which smash the cells. The vibration frequency is between 2000 and 4000 periods/min. The yeast cell suspension is generally subjected to this treatment for a few seconds to a few minutes. At a frequency of 4000 periods/min almost all the yeast cells are smashed after about 20 to 120 sec. After 120 sec at this frequency, e.g., only 0.05% of the yeast cells are not yet destroyed. During the grinding process the bottle containing the suspension is cooled externally, e.g. with carbon dioxide, so that the temperature in the cooled yeast suspension rises only minimally or not at all. The preferred temperature range which should prevail while the cells are being smashed is from about 0° to 5° C. The homogenate is separated from the undestroyed yeast cells, the cell walls and any cell membrane material by means of centrifuging and/or filtering. One obtains an extract of yeast cell contents.

The natural cell content substances, freed by the smashing (breaking open) of the cells, are analysed by means of protein determination, e.g. Bücher's biuret reaction. The measurement preferably ensues photometrically against a blank value, or else it is a UV measurement. The amount of protein is calculated e.g. according to the following relations:
mg protein in the cuvette contents = extinction × 17 or
mg protein/ml solution = 1.45·ext.$_{280}$ − 0.74·ext.$_{260}$
(280 = absorption maximum for proteins)
(260 = absorption maximum for DNS)

The enzyme activity of the wall-free yeast extract can be determined by the alcohol dehydrogenase activity (see "Biochemische Zeitschrift", Vol. 329 (1957), page 334).

The surprising effect of the extract of yeast cell contents according to the invention is attributed to the fact that one is dealing here with natural cell-content substances which, due to the careful treatment, are still fully effective; the effect of these substances on the skin is not only cumulative but, apparently by way of synergistically functioning substances of the cell nucleus, increases. If the yeast cell walls and/or the cell membranes are broken open mechanically, the proteins are not denatured, the vitamins not impaired and the desoxyribonucleic acids (DNS) and the repair complex of the yeast cell nucleus not destroyed. Such extracts of yeast cell contents have not as yet been used in the cosmetic industry. As may be gathered from the literature source "Kosmetologie" by Dr. J. S. Jellinek, page 105, yeasts have heretofore been of little significance to cosmeticians.

The entire, complex natural yeast cell contents are used as additive to cosmetic agents according to the invention. If, however, the cosmetic agent according to the invention is to have particularly good skin-regenerating properties, the natural yeast cell contents are subjected to further separation processes so as to enrich the fraction of yeast cell nuclei. The yeast cell nuclei fraction is especially rich in the nucleic acids of yeast and in the repair complex.

The mode of action of the repair complex of yeast cell nuclei is to be understood approximately as follows:

As a result of strong, incident UV light radiation, the DNS is damaged. This damage can be repaired by means of an endogenous protective system. It is assumed that the part of the DNS damaged by the UV radiation is repaired by the incorporation of new building elements and the intact strand of DNS thus closed again. It is assumed that the repair complex is able to accelerate the incorporation of new building elements. The active substance manufactured here from the yeast cell nuclei does not develop its effect in the connective tissue but at the lower cell layers of the epidermis. The cause of its effect is as yet unknown. It has in addition been found that the yeast cell nuclei fraction, which contains the repair complex, is impaired with respect to its repair capacity by the effect of heat. Incident sunlight thus promotes skin damage, which is caused by UV radiation. Thus, as experiment has shown, the new cosmetic agent increases the capacity of the skin cells to regenerate.

The cosmetic agent according to the invention contains natural yeast cell contents obtained by destroying the cell walls and breaking open the cells, the resulting extract of yeast cell contents being free of yeast cell walls and optionally free of nuclear membranes.

An embodiment of the invention is characterized by the addition of the yeast cell contents extract free of nuclear membranes. An other cosmetic agent of the invention contains the extract of yeast cell contents which consists of a natural extract of yeast cell nuclei.

It is advantageous to use the cell-content fractions A or B of example 1 and 2 correspondingly in a cosmetic agent of the invention, particularly in cosmetic agents such as a skin-care creme, agent for preventing sunburn, a face lotion, a facial tonic, a body lotion, a shaving lotion, make-up or bath oil.

The invention will now be explained with the help of the following examples:

EXAMPLE 1

810 g of baker's yeast were suspended in 750 g of tris buffer (tris(hydroxymethyl) amino methane buffer) with a pH of 8.0. The suspension was then ground, with simultaneous (2° C. to 4° C.) cooling, in a cell mill by means of glass balls measuring 0.2 to 0.5 mm in diameter. The throughput was adjusted such that 90% of the yeast cells were ground open. As cell mill, the Dynomill KDL was used. The suspension was then separated from cell wall fragments and non-destroyed yeast cells by subjecting it to centrifugation with 6000 g for 10 minutes. The upper fraction was diluted approximately 1:1 with tris buffer solution, producing a standardized solution with 1% protein. The standardized 1% yeast protein fraction had preservatives added to it and was then stored in the refrigerator at 4° C. for further processing.

This preparation A of yeast cell contents was processed to a cosmetic fluid or lotion of the following composition:

10000 wt. % of yeast cell content preparation A (standardized 1% protein)
7500 wt. % glycerin or sorbitol
7500 wt. % polyoxy-ethylated triglyceride
250 wt. % carboxyvinyl copolymer
60 wt. % preservative
7500 wt. % propanol-1
10000 wt. % polyethylene glycol
30 wt. % melissa oil to
1 00000 wt. % distilled water

EXAMPLE 2

20 g of baker's yeast were dried under vacuum for 48 hours and then suspended in 4% saline solution that contained 2% saccharose. After storing for 2 hours at 28° C. the yeast was separated from the liquid by means of a suction filter, and washed with distilled water. The remaining yeast was stirred in distilled water, in a ratio of 100 g wet yeast to 450 g water and with addition of enzymic glucoronidase/arylsulfatase (100000 Fishman units/1,000,000 Roy units), in a cell bomb at about 0° C. to about 5° C. for 1 hour under a pressure of 200 atmospheres of nitrogen. After depressurizing, the yeast cell nuclei were centrifuged down by addition of saccharose and ground in Bühler's cell mill by means of glass beads measuring 0.2 to 0.5 mm in diameter. After sedimenting down the glass beads, fraction B of yeast cell contents was obtained.

This yeast cell-content fraction B was incorporated in a cosmetic cream of the following composition:

10000 wt. % basic ointment substance
4000 wt. % decyloleate
4000 wt. % dodecyloleate
6000 wt. % maize germ oil
1000 wt. % cholesterol
1000 wt. % bees wax
6000 wt. % isopropylmyristate
1000 wt. % polyoxy-ethylated triglyceride
4000 wt. % paraffin oil 3000 wt. % sorbit
200 wt. % magnesium sulphate
50 wt. % preservatives
200 wt. % panthenol
100 wt. % scenting agent
10000 wt. % yeast cell-content fraction B (standardized 1% protein) to
100000 wt. % distilled water

EXAMPLE 3

Example for Application

The skin lotion according to Example 1 was adjusted so as contain firstly 5 wt. % and secondly 10 wt. %, relative to the entire weight of the lotion, of yeast preapration A (standardized to 1% protein); the effect of these two lotions on rough, scaly and dry skin was then examined by applying the lotions to several parts of the correspondingly-prepared hands of test persons. The hands of the test persons had been treated with a lime-cement mixture prior to applying the lotions, so as to make them rough, scaly and dry. On treatment with the test lotions of the invention, the outward appearance of the treated skin parts returned to normal immediately. The effect was described by the test persons as pleasantly soothing. The blood supply to the upper layer of skin was stimulated. The skin tonus was improved, and the surface of the skin acquired a pleasant softness. In the case of the lotion containing 5 wt. % of yeast preparation A according to the invention, the roughness of the skin became evident again, to a much reduced degree, after 4 to 6 hours. In the case of the lotion containing 10 wt. % of yeast preparation A the skin roughness did not reappear even after a period of 10 hours of observation.

EXAMPLE 4

Control Experiment

The skin lotion of Example 1, which contained yeast preparation A, was adjusted to contain 10 wt. % of the latter. The effect this lotion had on the skin of 24 test persons was then examined. As a control experiment, the same skin lotion was prepared but contained, instead of the yeast preparation A according to the invention, the same amount of untreated baker's yeast.

The skin lotion or fluid of the invention was recognized as having a significant effect on the skin of all 24 test persons. This lotion soothed and smoothed the skin, and increased the moisture content of the upper layer of skin notably. A corresponding effect on the skin of the test persons was not obtained with the control fluid, which contained only untreated baker's yeast.

What is claimed is:

1. A cosmetic agent suitable for application to the skin comprising the usual basic cosmetic substances, and natural extract of yeast cell contents obtained by destroying yeast cell walls and breaking open yeast cells, the resulting natural extract of yeast cell contents being free of yeast cell walls in an amount in the range of 2 to 20 wt. % for the extract of yeast cells based upon the total weight of the cosmetic agent.

2. Cosmetic agent according to claim 1, characterized in that the extract of yeast cell contents obtained is largely free of nuclear membranes.

3. Cosmetic agent according to claim 1, characterized in that the extract of yeast cell contents comprises 5 to 10 wt. % of the cosmetic agent, relative to the total weight thereof.

4. Cosmetic agent according to claim 1, characterized in that, besides the natural extract of yeast cell contents, it contains at least one of the compounds selected from the group consisting of glycerin, polyoxy-ethylated triglyceride, carboxyvinyl copolymer, preservatives, propanol, polyethylene glycol, distilled water, a scenting agent, carboxymethyl cellulose, bees wax, maize germ oil, cholesterol, paraffin oil, magnesium sulfate and decyloleate.

5. Cosmetic agent according to claim 1 comprising the following composition:
10000 wt. % of yeast cell content preparation A of example 1
7500 wt. % glycerin or sorbitol
7500 wt. % polyoxy-ethylated triglyceride
250 wt. % carboxyvinyl copolymer
60 wt. % preservative
7500 wt. % propanol-1
10000 wt. % polyethylene glycol
30 wt. % melissa oil
to 100000 wt. % distilled water.

6. A method for manufacturing a cosmetic agent containing yeast in addition to usual basic cosmetic substances, comprising the steps of simultaneous cooling yeast cells, smashing the yeast cells by mechanical means at a temperature of about 0° C. to about 5° C., separating off by means of at least one of centrifuging and filtering at a temperature of 0° C. to about 5° C., the non-destroyed yeast cells, the yeast cell walls and any yeast cell nuclear membranes and combining the resulting natural extract of yeast cell contents together with the usual basic cosmetic substances to form a cosmetic agent.

* * * * *